United States Patent
Hacker et al.

(10) Patent No.: US 9,649,024 B2
(45) Date of Patent: May 16, 2017

(54) METHOD FOR THE MODEL-BASED DETERMINATION OF THE BIOMETRY OF EYES

(75) Inventors: Martin Hacker, Jena (DE); Ferid Bajramovic, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 77 days.

(21) Appl. No.: 13/884,827

(22) PCT Filed: Nov. 9, 2011

(86) PCT No.: PCT/EP2011/005615
§ 371 (c)(1),
(2), (4) Date: Jul. 17, 2013

(87) PCT Pub. No.: WO2012/062453
PCT Pub. Date: May 18, 2012

(65) Prior Publication Data
US 2013/0301009 A1 Nov. 14, 2013

(30) Foreign Application Priority Data
Nov. 12, 2010 (DE) .......................... 10 2010 051 281

(51) Int. Cl.
*A61B 3/00* (2006.01)
*A61B 3/10* (2006.01)
*G01B 9/02* (2006.01)

(52) U.S. Cl.
CPC .......... *A61B 3/102* (2013.01); *G01B 9/02063* (2013.01); *G01B 9/02089* (2013.01); *G01B 9/02091* (2013.01); *A61B 3/1005* (2013.01)

(58) Field of Classification Search
CPC ......... A61B 3/102; A61B 3/14; A61B 3/0025; A61B 3/12; A61B 3/113; A61B 3/0008;
(Continued)

(56) References Cited

U.S. PATENT DOCUMENTS

| | | |
|---|---|---|
| 5,321,501 A | 6/1994 | Swanson |
| 5,347,328 A | 9/1994 | Sekine |
| (Continued) | | |

FOREIGN PATENT DOCUMENTS

| | | |
|---|---|---|
| DE | 43 09 056 A1 | 9/1994 |
| DE | 198 12 297 C2 | 9/1999 |
| (Continued) | | |

OTHER PUBLICATIONS

Cai, Yiyu, et al. "Parametric eyeball model for interactive simulation of ophthalmologic surgery." Medical Image Computing and Computer-Assisted Intervention—MICCAI 2001. Springer Berlin Heidelberg, 2001.*
(Continued)

*Primary Examiner* — Scott J Sugarman
*Assistant Examiner* — Sharrief Broome
(74) *Attorney, Agent, or Firm* — Patterson Thuente Pedersen, P.A.

(57) ABSTRACT

For the model-based determination of the biometry of eyes, the eye is illuminated by a light source via a scanning unit, the focus of the measuring light beam in the eye is moved or shifted laterally and/or axially via an adjusting device and the light fractions back-scattered by the boundary surfaces and from the tissue of the eye via an interferometer are detected by a sensor and relayed to a control and evaluation unit by which a parametric eye model which describes at least two boundary surfaces present in the eye is adapted to the scan or scans. The invention relates to the field of ophthalmology and serves in particular for the optical determination of the biometry of eyes by application of two-dimensional optical coherence tomography images. However, the method is not limited to the use of coherence tomography nor to the utilization of optical measurements.

12 Claims, 3 Drawing Sheets

B-SCAN OF AN EYE WITH SCANNING WITH OF 10 mm

Figure 1:
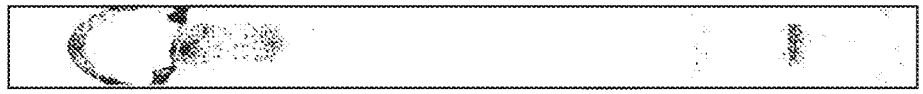

(58) Field of Classification Search
CPC ..... A61B 3/0091; A61B 3/1015; A61B 3/107;
A61B 3/145; A61B 3/0041; A61B
3/1005; A61B 3/1025; A61B 3/0058;
A61B 3/10; A61B 3/103; A61B 3/152;
A61B 3/00
USPC ................................. 351/205, 208, 212, 246
See application file for complete search history.

(56) References Cited

U.S. PATENT DOCUMENTS

| | | | |
|---|---|---|---|
| 6,268,921 B1 | 7/2001 | Seitz | |
| 6,377,349 B1 | 4/2002 | Fercher | |
| 2004/0165146 A1* | 8/2004 | Della Vecchia | A61B 3/12 351/221 |
| 2006/0158655 A1 | 7/2006 | Everett | |
| 2007/0046948 A1* | 3/2007 | Podoleanu | A61B 3/102 356/497 |
| 2007/0291277 A1 | 12/2007 | Everett | |
| 2008/0198329 A1* | 8/2008 | Gaida | A61B 3/0025 351/205 |
| 2008/0309881 A1 | 12/2008 | Huang | |

FOREIGN PATENT DOCUMENTS

| | | |
|---|---|---|
| DE | 101 08 797 A1 | 9/2002 |
| DE | 103 60 570 A1 | 7/2005 |
| DE | 10 2008 063225 A1 | 7/2010 |
| DE | 10 2009 007732 A1 | 8/2010 |
| EP | 1 941 456 B1 | 7/2008 |
| WO | WO 2004/071286 A1 | 8/2004 |
| WO | WO 2010/028654 A1 | 3/2010 |
| WO | WO 2010028654 * 3/2010 ............. A61B 3/117 | |
| WO | WO 2010/070020 A2 | 6/2010 |

OTHER PUBLICATIONS

A. F. Fercher, et al.; "Measurement of optical distances by optical spectrum modulation"; Proc. SPIE vol. 2083, 263-267, 1993.

A. F. Fercher, et al.; "In Vivo Optical Coherence Tomography in Ophthalmology"; Bellingham, SPIE. pp. 355-370, ISBN 0-8194-1379-8, 1993.

A. F. Fercher et al.; "Measurement of intraocular distances by backscattering spectral interferometry"; Opt. Commun. 117 (1995), 43-48.

G. Häusler and M. W. Lindner; "'Coherence RADAR' and 'spectral RADAR'—New tools for dermatological diagnosis"; J. Biomed. Opt. 3(1), 21-31, 1998.

A. G. Podoleanu, J. A. Rogers, D. A. Jackson, and S. Dunne; "Three dimensional OCT images from retina and skin"; Opt. Express, 7, 2000, pp. 292-298.

S. Radhakrishnan et al.; "Real time optical coherence tomography of the anterior segment using hand-held and slit-lamp adapted systems"; Proc. SPIE 4619, 227-229, 2002.

R. Huber et al.; "Three-dimensional and C-mode OCT imaging with a compact, frequency swept laser source at 1300 nm"; Optics Express, vol. 13, No. 26, Dec. 26, 2005, 10523-10538.

* cited by examiner

B-SCAN OF AN EYE WITH SCANNING WITH OF 10 mm

ANTERIOR OF B-SCAN OF FIG.1

A-SCAN COMPUTED FROM
10 CENTRAL A SCANS BY AVERAGING

METHOD FOR THE MODEL-BASED DETERMINATION OF THE BIOMETRY OF EYES

RELATED APPLICATIONS

The present application is a National Phase entry of PCT Application No. PCT/EP2011/005615, filed Nov. 9, 2011, which claims priority from DE Application No. 10 2010 051 281.8, filed Nov. 12, 2010, which applications are hereby incorporated by reference herein in their entirety.

FIELD OF THE INVENTION

The present invention relates to the field of ophthalmology, in particular the determination of a plurality of lengths and other variables based on localized boundary surfaces in the eye. Two-dimensional optical coherence tomography recordings (B scans) are preferably used for this purpose.

BACKGROUND

Although biometry, also referred to as biometrics, is generally concerned with measurements and the measuring and evaluation processes necessary for this purpose in organisms, in the following discussion it is not limited strictly to eyes.

A number of methods and measuring devices are known in the prior art for determining the known features of the structures of an eye; in this regard, primarily ultrasonic measuring devices and optical measuring devices based on short coherent interferometric methods or confocal scanners have become established. Of the numerous approaches known from the prior art, the medical-diagnostic importance of the mentioned measurements is evident.

A number of methods and measuring devices are known in the prior art for determining the known features of the structures of an eye; in this regard, primarily ultrasonic measuring devices and optical measuring devices based on short coherent interferometric methods or confocal scanners have become established.

The specific disadvantages of ultrasonic devices are, on the one hand, lower resolution, and on the other hand, the need for direct contact with the eye, which always entails the risk of transmission of infections, and also requires that the eye be anesthetized for the measured value determination. In ultrasonic devices there is no automatic alignment of the measuring beam on the visual axis of the eye, so that the likelihood of erroneous measurements is accordingly high.

Analogously to the ultrasonic devices, in which images of the structural transitions are reconstructed based on the acoustic signals, in the optical measuring devices based on short coherent interferometric methods, optical images of the structural transitions are represented as one-dimensional depth profiles (A scans) or two-dimensional depth section images (B scans). As a short coherent measuring method, the so-called optical coherence tomography (OCT) method has become established, in which coherent light is used for distance measurement of reflective and scattering materials with the aid of an interferometer. For depth scanning, optical coherence tomography for the human eye provides signal responses which are measurable at optical boundary surfaces due to changes in the refractive index.

The basic principle of the OCT method described in U.S. Pat. No. 5,321,501 A, for example, is based on white light interferometry, and compares the propagation time of a signal, using an interferometer (usually a Michelson or Mach-Zehnder interferometer). The arm having a known optical path length (also referred to as the reference arm) is used as a reference with respect to the measuring arm. The interference of the signals from the two arms produces a pattern from which the relative optical path length within an A scan (individual depth signal) may be read. In the one-dimensional raster process, the beam, analogously to ultrasonic technology, is then guided transversally in one or two directions, by means of which a flat B or C scan or a three-dimensional tomogram may be recorded.

In the OCT method used in ophthalmology, two different types have become established. For determining the measured values, in the first type the length of the reference arm is changed, and the intensity of the interference is continuously measured without taking the spectrum into account. This method is referred to as the "time domain" method. In contrast, in the other method, referred to as the "frequency domain" method, for determining the measured values the spectrum is taken into account and the interference of the individual spectral components is detected. Therefore, reference is made on the one hand to the signal in the time domain, and on the other hand, to the signal in the frequency domain. The advantage of the "frequency domain" method lies in the simple and rapid simultaneous measurement, in which complete information concerning the depth may be determined without necessarily requiring moving parts. This increases the stability and the speed. Due to the Fourier transform used for reconstructing the position information, these methods are also referred to as "Fourier domain" methods.

The "frequency domain" method may be divided into simultaneous methods and sequential methods, depending on the light source used. The simultaneous method, which requires a broadband light source such as a superluminescent diode (SLD) or a femtosecond laser, is also referred to as a "(parallel) spectral domain" method. In contrast, in the sequential method a tunable light source having a variable wavelength is used, the sequential "frequency domain" method also being referred to as the "swept source" (SS OCT) method. Common "swept source" light sources are tunable lasers which use rapidly variable spectral filters such as the Fabry-Perot filter, or wavelength selectors based on rotating polygon scanners, or also current-tunable semiconductor lasers. The tuning rates may be in the range of several hundred hertz to several megahertz.

In contrast, the "time domain" method may be divided into simultaneous methods and sequential methods, depending on the detector used, a broadband light source always being used. Whereas in the simultaneous "time domain" method the expanded measuring beam strikes a diode, CCD array, or CMOS array (full-field OCT), in the sequential "time domain" method the measuring beam is deflected onto a simple high-sensitivity photodiode via an interferometric beam splitter and a displaceable mirror in the reference arm. When an OCT scan is recorded at a constant setting of the reference arm, this is referred to as the performance of a C scan or an "enface OCT." However, the term "enface OCT" is also sometimes used for the frontal views obtained from OCT volume scans.

The major technological advantage of OCT is the decoupling of the depth resolution from the transversal resolution. The depth resolution is determined only by the utilized bandwidth of the light source used. Common bandwidths are in the range of several nanometers to over one hundred nanometers, and when measuring radiation in the near infrared is used, 700-1350 nm. The depth resolutions thus achievable are in the range of 3-100 μm. In contrast to microscopy, the three-dimensional structure of the object to be examined may thus be detected, even when the numerical aperture, for example for small pupils in nondilated eyes, is greatly limited.

The purely reflective, and therefore contactless, measurement allows the generation of microscopic images of living tissue (in vivo). The wavelength of the measuring radiation to be used is determined by the desired application, taking into account the wavelength-dependent tissue absorption and back-scattering. If the ocular fundus, for example, is to be measured, in particular radiation in the range of 690-900 nm or 960-1100 nm is suited, and for the anterior portion of the eye, for example radiation in the range of 1260-1360 nm is suited.

The approach for eye diagnosis described in U.S. Pat. No. 5,347,328 A is based on the interferometric measurement of the length of the optical axis of an eye. For this purpose, the eye is illuminated with a coherent light beam whose wavelength is varied in a predetermined range. The change in the wavelength causes a change in the phase difference of the beams reflected on the boundary surfaces, which is used for determining the distance between the corneal surface and the ocular fundus.

The publication [1] by A. F. Fercher et al. describes the Fourier optical OCT method in general, and publication [2] also describes the specialized determination of the coherence function of the light reflected from the eye by inverse Fourier transformation of the spectral intensity distribution.

Use of the Fourier transform method in particular for measuring intraocular distances along a single beam through the pupil has been described by A. F. Fercher et al. in publication [3], and used by G. Häusler and M. W. Lindner according to publication [4] for producing OCT images.

DE 43 09 056 A1 describes a method for determining the distance and scattering intensity of scattering points, in which the distance and the local scattering intensity are determined by Fourier transformation of the spectrum according to the wavelength.

A method in which three-dimensional images of the retina may be synthesized from enface OCT recordings has been described by A. G. Podoleanu, J. A. Rogers, D. A. Jackson, and S. Dunne in publication [5].

A parallel OCT method which likewise uses a stepped reference mirror is described in U.S. Pat. No. 6,268,921 B1. The stepped reference mirror is used to achieve the depth scan in so-called time domain OCT. Accordingly, the step increments are much greater than $\lambda/8$. In addition, the steps are distributed not with periodically recurring overall heights, but, rather, over the entire surface in a stepped manner. The phase shifter which is also used in this approach acts equally on the entire reference arm or measuring arm. These differences naturally result from the other statement of the object also contained in the cited document.

A similar method based on piezoelectric phase shifting phase measurement is the subject of U.S. Pat. No. 6,377,349 B1. In this approach, the reference mirror is piezoelectrically displaced. However, this displacement and the necessary additional illumination, as well as the multiple readout of the photodetector array, are time-consuming, which results in motion artifacts in living objects such as the eye.

A conventional OCT method for determining the dimensions of the anterior portions of the eye, using a slit lamp and a hand-held device, has been described by S. Radhakrishnan et al. in publication [6]. The device, which is based on time domain OCT, operates very quickly, delivering 8 images per second. For example, for a three-dimensional representation of the anterior eye structure, the 8 images per second may be distributed equidistantly over the entire pupil, in which case approximately 1 second is required for the data recording.

In the optical measuring devices based on short coherent methods, the interferometer principle according to the dual beam method is also used. This method is characterized in particular by insensitivity to axial eye movements, since use is made of an interference between the light components reflected from the cornea and back-scattered by other eye structures. Approaches based on this measuring principle are described, for example, in DE 198 12 297 C2, DE 103 60 570 A1, and WO 2004/071286 A1.

As a result of the OCT methods as well as the noninterferometric confocal methods (US 2006/0158655 A1), accurate values of axial distances in optical path lengths are obtained. While the deviations in the OCT methods are less than the coherence length, the deviations in the confocal methods, depending on the quality of the scattered light suppression, are somewhat less favorable, but likewise are still in the submicron range. In the OCT methods it is particularly advantageous that interferometric measurements of optical path lengths may be carried out using very precise and stable external references, in particular also by measuring reference structures, or using reference interferometers for implementing a so-called k-clock [7].

One of the authors of the present patent application has previously published on various devices and methods for achieving improved, more stable signal strengths in the various regions of the eye, the contents of which are referenced below. This relates in particular to the approaches for improved performance of fixing marks (according to DE 10 2009 007732 A1), for changing focus positions (according to WO 2010/017954 A1), and for adapting reference planes (according to DE 10 2008 063225 A1).

Reproducible distance measurements having sufficiently good resolution and signal strength of media in the eye, for example corneal boundary surfaces or retinal layers, may be ensured by these methods. The refractive indices of the optical media, such as the cornea, the aqueous fluid, the lens, and the vitreous body, are sufficiently well known, and are defined, for example, in the Gullstrand eye model.

Furthermore, reference is likewise made to the two patents DE 101 08 797 A1 and EP 1 941 456 B1, relating to the automatic scanning evaluation of interferometric measurements of the eye for distance determination in eye structures.

In the approaches known from the prior art, section images of the media of the eye are generated by multiple, successively applied so-called depth scans, resulting in 3D representations. Depth scans or A scans for generating section images of the eye provide exact measured values, regardless of whether the scan is performed centrally through the pupil or at the pupil margin. Depending on the orientation of the eye, the scans may be performed in the direction of the optical axis, the visual axis, or any other given axis of the eye. The determined optical path lengths are converted into path lengths in the medium by means of the group refractive index of the particular optical media, taking into account the wavelength of the measuring radiation used.

A problem with the known approaches is that automatic evaluations of A and B scans for collecting biometric data are confronted with a number of measuring situations and interferences, in spite of which the automatic evaluations must still function accurately and with a minimum number of defects. Examples are eye length measurements in preparation for IOL implants in the treatment of cataracts, or severe refractive errors, or the replacement of IOLs.

In these cases, very different measuring conditions are present under which automatic scanning evaluation and collection of biometric data from OCT scans must reliably function, such as measurement radiation attenuation in cataracts, or measurement radiation defocusing in the case of refractive error, or also the presence of pathologies such as retinal edema. In the prior art this has been achievable only to a very limited extent, for which reason measured value deviations or incomplete measurement evaluations occur, which then require manual corrections of the distance measurements, which themselves may likewise contain errors.

LITERATURE

[1] A. F. Fercher, et al.; "Measurement of optical distances by optical spectrum modulation"; Proc. SPIE Vol. 2083, 263-267, 1993
[2] A. F. Fercher, et al.; "In Vivo Optical Coherence Tomography in Ophthalmology"; Bellingham, SPIE. pp. 355-370, ISBN 0-8194-1379-8, 1993
[3] A. F. Fercher et al.; "Measurement of intraocular distances by backscattering spectral interferometry"; Opt. Commun. 117 (1995), 43-48
[4] G. Häusler and M. W. Lindner; "'Coherence RADAR' and 'spectral RADAR'—New tools for dermatological diagnosis"; J. Biomed. Opt. 3(1), 21-31, 1998
[5] A. G. Podoleanu, J. A. Rogers, D. A. Jackson, and S. Dunne; "Three dimensional OCT images from retina and skin"; Opt. Express, 7, 2000, pp. 292-298
[6] S. Radhakrishnan et al.; "Real time optical coherence tomography of the anterior segment using hand-held and slit-lamp adapted systems"; Proc. SPIE 4619, 227-229, 2002
[7] R. Huber et al.; "Three-dimensional and C-mode OCT imaging with a compact, frequency swept laser source at 1300 nm"; OPTICS EXPRESS, Vol. 13, No. 26, Dec. 26, 2005, 10523-10538

SUMMARY OF THE INVENTION

The invention includes a method for determining a plurality of lengths and other variables in the eye which remedies the disadvantages of the approaches known from the prior art and which, with the greatest possible ease of operation, provides a large number of reproducible and evaluatable measured values, in particular also under non-ideal conditions. By use of the method according to an embodiment of the invention, the aim is to be able to determine, preferably from only one scanning sequence, the greatest possible number of measured values with maximum reliability in order to minimize the frequency of inaccurate or unevaluatable measurements, and thus, the measuring time imposed on the patient.

Using the method according to an embodiment of the invention for model-based determination of the biometry of eyes, based on optical coherence tomography (OCT), in which the eye is illuminated by a light source via a scanning unit, the focus of the measuring light beam in the eye is movable or switchable laterally and/or axially by means of an adjusting device, and the light components back-scattered from the boundary surfaces and from the tissue of the eye are detected by a sensor via an interferometer and relayed to a control and evaluation unit, the scanning unit performs one or more scans having the same or different scan patterns, and/or the same or different focus settings, and the scans are received by the sensor via the interferometer and relayed to a control and evaluation unit which adapts a parametric eye model, which includes at least two boundary surfaces present in the eye, to the scan or scans, derives the biometric measured values from the model, and represents individual or all scans and/or the adapted eye model via a user interface.

The present approach relates to the general field of ophthalmology, and is used in particular for the optical determination of the biometry of eyes by application of two-dimensional optical coherence tomography recordings. In principle, however, the method in general is not limited to the use of coherence tomography, or to the use of optical measurements.

Figure 2:
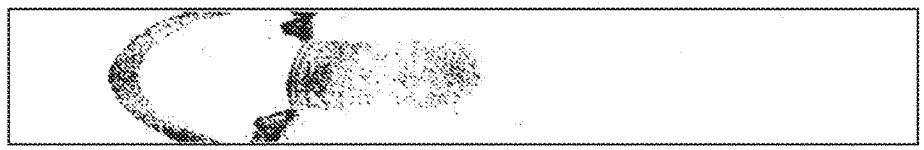
Figure 3:
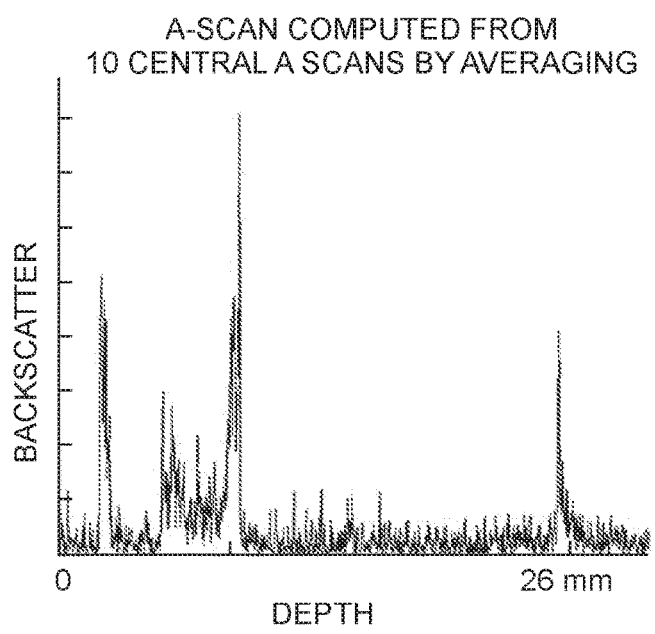
Figure 4:
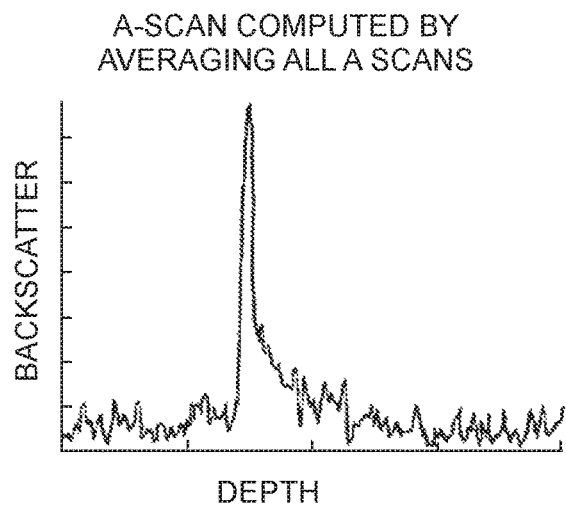
Figure 5:
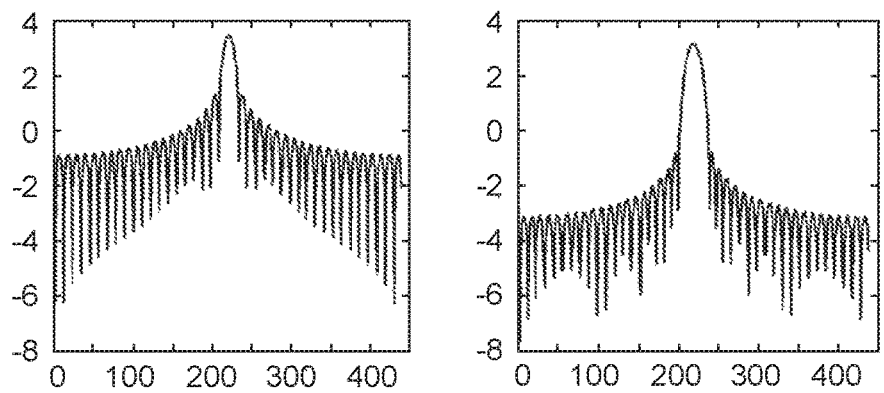
Figure 6:
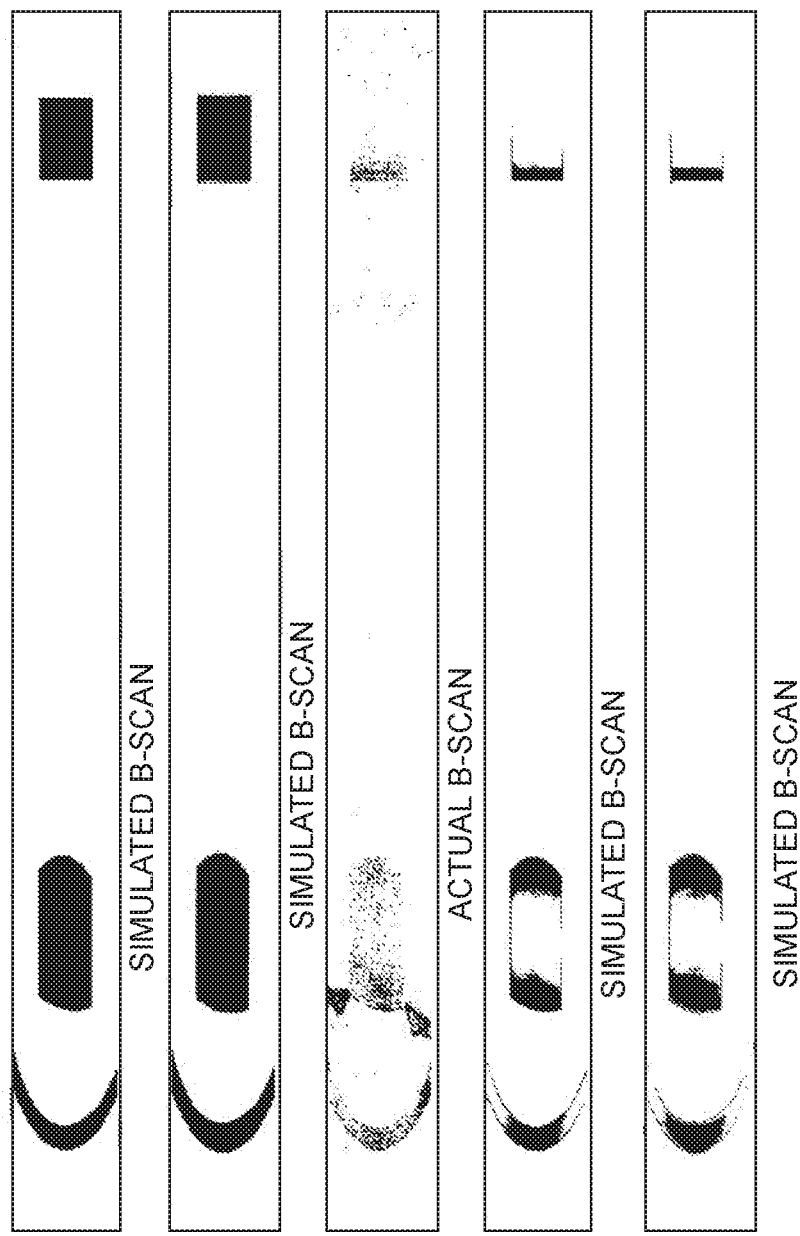

The invention is described in greater detail below with reference to exemplary embodiments, for which the figures show the following:

FIG. 1: depicts a B scan having an anterior focus and an anterior reference plane, with a scanning width of 10 mm, FIG. 2: depicts the anterior portion of the B scan according to FIG. 1, FIG. 3: depicts an A scan computed from 10 central A scans by averaging, FIG. 4: depicts a detail of an A scan computed by averaging all A scans, FIG. 5: depicts two different point spread functions, and FIG. 6: depicts a comparative illustration of multiple simulated B scans and one actual B scan.

DETAILED DESCRIPTION

In the method according to an embodiment of the invention for the model-based determination of the biometry of eyes, based on optical coherence tomography (OCT), the eye is illuminated by a light source via a scanning unit, the focus of the measuring light beam in the eye is moved or switched laterally and/or axially by application of an adjusting device, and the light components back-scattered from the boundary surfaces and from the tissue of the eye are detected by a sensor via an interferometer and relayed to a control and evaluation unit. The control and evaluation unit adapts a parametric eye model, which describes at least two boundary surfaces present in the eye, to the scan or scans, derives the biometric measured values from the model, and represents individual or all scans and/or the adapted eye model via a user interface.

The adaptation of the parametric eye model to the scan or scans is carried out in such a way that the model describes the actual structures of the eye with a high degree of certainty, in the sense that for at least one value which is computable from the model (for example, a value listed above), the deviation from at least one alternative measurement using a different method (for example, an ultrasonic or optical biometry device) is at most 20% in at least one eye. This requires that all OCT scans used are sufficiently well calibrated in the depth direction and in the lateral direction, which may be achieved by measuring reference objects for determining scaling factors or scaling functions.

Depending on the OCT method, the mentioned sensor may be fast photodiodes, balanced detectors, or also spectrometers. Polygon scanners, microelectromechanical scanners (MEMS), or preferably pairs of galvo scanners are suited as scanning units.

The scan patterns may be, for example, linear or planar scan shapes (curves, cylinders) as well as volume scans, or combinations thereof. OCT information may then be collected on the mentioned surfaces by means of these scan patterns. Various designs are suitable for interferometers, for example Michelson or Mach-Zehnder interferometers in free beam or fiber optic designs.

The light source is a source which is adapted to the particular OCT method, for example a broadband superluminescent diode for carrying out high-resolution TD-OCT or SD-OCT, or an ultrafast tunable laser for carrying out SS-OCT.

In a first method step, the scanning unit for example performs one or more B scans in the form of partial or whole eye scans which include at least two of the boundary surfaces present in the eye. These scans are received by the sensor via the interferometer and relayed to a control and evaluation unit. Relevant boundary surfaces are, among others, the anterior and posterior boundary surface of the cornea and of the lens, the internal limiting membrane, the anterior side of the retinal pigment epithelium, and the anterior side of the iris.

In a second method, the control and evaluation unit adapts a parametric eye model to the performed scans. This is carried out by comparison (pixel-by-pixel, for example) of the scan to a simulated scan according to the parametric eye model and/or by fitting functions. It is immaterial whether the scans image the entire eye or only a portion thereof, for example the anterior portion.

The parametric eye model preferably represents the relevant boundary surfaces of the eye by application of functions, for example polynomials. These may for example be one-dimensional (1D) functions for two-dimensional modeling of the eye (in particular in the case of one or more B scans in the same plane), or two-dimensional functions for three-dimensional modeling of the eye (in particular in the case of multiple B scans in various planes).

After the model is adapted to the scan or scans, various values may be computed from the model parameters, in particular the values listed above.

In this regard, FIG. 1 shows a B scan having an anterior focus and an anterior reference plane, with a scanning width of 10 mm. In contrast, FIG. 2 shows only the anterior portion of the B scan according to FIG. 1.

Since the visibility of certain eye structures, such as the lens or the retina, is essentially dependent on the recording technique used, the visibility may be varied by changing the scan patterns and/or the focus setting. In addition to scans in the form of partial or whole eye scans, the evaluation may also be based on a synthetic whole eye scan which has been computed from multiple B scans using different measurement modalities.

The core concept of the method according to the invention is the use of a parametric eye model which is two- or three-dimensional, and which partially or completely models the portions of the eye which may be resolved using optical coherence tomography. The model parameters may describe, among other things, geometric aspects such as the location and shape of boundary surfaces, and the state of the eye. Part of the model parameters may be predefined, for example using a measuring unit and/or input unit and/or data transmission unit which is/are additionally present. In addition to keyboards or the like, these units are understood to be data carriers, networks, or measuring modules integrated into the system. These model parameters may be known, or may have been determined using other measuring methods.

Since various information and data concerning in particular the state of the eye to be measured are generally already present or may be easily determined, it is particularly advantageous to include these in the determination of the biometry. Known information and data may include the following aspects, among others:

Refractive error,
State of the lens of the eye (phakic, aphakic, or pseudophakic),
Nature (type and material, for example) and optionally location (for example, capsular bag and/or anterior chamber) of the intraocular lens(es), if present,
Presence of a contact lens,
Cataracts and their degree and type,
Prior treatments of the cornea (for example, LASIK, keratoplasty, etc.),
Pathologies (for example, hemorrhaging, retinal detachment, or macular edema).

The method according to the invention uses a parametric model of the eye which is additionally configurable by the user, in that knowledge about the state of the eye and/or measured values from other measuring methods may be taken into account.

These inputs and additional information are used for the automatic evaluation, and may therefore be provided before or after the recording. The aim of using a preferably global configurable model is to reduce the influence of noise and artifacts in the recordings, and to improve the reproducibility and the yield of successfully evaluatable recordings.

An important aspect of the configurability of the eye model is that the inputs and additional information may already be used for adapting the eye model to the scan or scans. This is reflected in the fact that a representation of the eye model, for example as a superimposition of the scan or scans, may change, depending on the configuration of the eye model. Thus, the configurability in particular goes beyond mere correction of measured values, for example based on a refractive index which is a function of the state of the eye. For example, in the adaptation of the eye model to the scan as a function of the configuration, the lens of the eye may be taken into account (phakic eye) or excluded (aphakic eye). The adaptation of the eye model to the scans may thus be speeded up and/or made more robust and less susceptible to error. For this purpose, configuration-dependent characteristics of expected signals may be taken into account, for example the position, extent, and intensity of OCT reflections from artificial lens boundary surfaces in the case of the configuration of pseudophakic eyes.

The above-mentioned measuring variables, such as length of the eye or depth of the anterior chamber, may be part of the model parameters, or may be computed therefrom in a separate step.

Although the configurability of the eye model is based primarily on the state of the eye, which in practice is often known and input by the user, in the broader sense the use of additional measurement techniques may also be regarded as configurability. This may involve, for example, keratometry or topography of the anterior side of the cornea, for which the shape of the anterior side of the cornea is known. Such measurements may be handled in an exact manner (compared to the resolution of the OCT scan) or as approximations. For use as approximations, smaller deviations of the corresponding model parameters are allowed. For use as exact prior knowledge, the corresponding model parameters are not changed in the adaptation of the model to the scan or scans.

In addition to the anatomical structures, the eye model may include the movement of the eye during the measuring process. This movement may be modeled, for example, as a constant speed and/or acceleration. Additional measuring techniques are helpful for a reliable estimation of the (at least axial) eye movement.

In another method step according to the invention, the control and evaluation unit generates simulated OCT scans for the parametric eye model which are compared to the actual OCT scans, the determined deviation being used as a quality criterion of the model parameters or as a target function. In the generation of simulated OCT scans, the control and evaluation unit may take sources of error into account in the signal generation, the signal recording, and the signal processing. The simulated OCT scans generated by the control and evaluation unit for the eye model establish a reference between the eye model and the actual OCT scans.

In the generation of simulated OCT scans, the control and evaluation unit may take the following sources of error, for example, into account:

Exponential drop of the signal in the tissue in the axial direction, in particular in the retina, Artifacts in the signal resulting from window effects in the Fourier transform, Artifacts in the scans produced by the light source, Artifacts which appear from the interferometer at constant positions, independently of the useful signal, Reflected and/or blurred OCT signals, Overload of the detector caused by measuring light beams striking perpendicularly on a boundary surface, and Refraction of the measuring light beams produced at the boundary surfaces of the eye.

The exponential drop of the signal in the tissue in the axial direction is noted in particular in the retina. In this regard, FIG. 3 shows an A scan which has been computed by averaging the central 10 A scans according to FIG. 1. For improved clarity, FIG. 4 shows a detail of an A scan around the retina which has been computed by averaging all A scans that include the retina. The signal drops exponentially behind the main peak.

The artifacts in the signal caused by window effects in the Fourier transform result in a nonideal point spread function. In this regard, FIG. 5 shows two different point spread functions resulting from use of the Kaiser-Bessel window, having parameters $\beta=2$ (left) and $\beta=4.5$ (right). In contrast, an ideal point spread function would be composed of a single peak having a width of zero; in practice, however, there is a trade-off between the width of the main peak and the height of the side lobes. In the generation of simulated OCT scans, the actual signal results from convolution of the ideal signal (A scan) with a point spread function.

In the generation of simulated OCT scans, the control and evaluation unit may likewise model by convolution the artifacts possibly produced in the A scans by the light source, for example due to interfering reflections inside the source.

The artifacts which appear from the interferometer at constant positions, independently of the useful signal, may be taken into account in the evaluation of the actual scans by ignoring these as so-called "expected" errors.

Reflected and/or blurred OCT signals and overload of the detector caused by measuring light beams striking perpendicularly on a boundary surface may also be regarded as "expected."

The refractions of the measuring light beams produced at the boundary surfaces of the eye may be taken into account by the control and evaluation unit in the generation of simulated OCT scans by using ray tracing techniques.

The control and evaluation unit may represent simulated B scans discretely or continuously. The simulation may describe realistic or simplified signal intensities or their probabilities. The intensity curve within the eye model and the corresponding probabilities may be explicitly modeled, or automatically or partially automatically learned from actual scans.

In this regard, FIG. 6 shows a comparative illustration of multiple simulated B scans and one actual B scan. The topmost illustration shows a simulated B scan having binary intensities, while the B scan illustrated immediately underneath contains an additionally simulated point spread function (having intense side lobes). An actual B scan according to FIG. 1 is illustrated in the middle. The scan illustrated immediately underneath once again shows a simulated B scan having a roughly approximated intensity distribution, which ultimately, as shown in the bottommost illustration, contains an additionally simulated point spread function.

As described above, in this method step the simulated OCT scans generated by the control and evaluation unit for the parametric eye model are registered with the actual OCT scans, the determined deviation being used as a quality criterion of the model parameters or as a target function.

The quality criterion or the target function quantifies how well a certain set of model parameters registers the simulated and actual scans with one another. The quality criterion or the target function may contain additional knowledge, such as the requirement that certain boundary surfaces are (approximately) convex or concave.

The quality criterion or the target function may carry out a direct comparison of an actual B scan and a simulated B scan by correlation, for example. In this regard, a model of the noise may be used. It is also possible to combine different preprocessed B scans, for example to weight edges more strongly. If the simulated scan represents intensity probabilities, the target function assesses the probability of the actual scan with respect to the given intensity probabilities.

Either a single B scan, or multiple B scans simultaneously, may be processed in the registration. The relationship between multiple B scans represents the shared eye model. Thus, for example, a set of B scans along various meridians (preferably having known meridian angles) and/or various recording modes, for example anterior chamber scans and retina scans, may be processed together. In the latter case, the eye model may include all structures which, taken together, are visible in all scans. However, a suitable scanner model is used in each case, depending on the recording mode.

The shared processing of multiple scans assures further improvement of the repeatability, provides a 2D or 3D registration of the individual scans with respect to one another by means of the shared eye model, and allows the preferences of various recording modes to be combined.

In another method step, the quality criterion or the target function is optimized by the control and evaluation unit, so that the simulated scans may be harmonized with the actual OCT scans.

The selection of the search, optimization, or solution process for (approximate) determination of the global optimum of the target function depends on the mathematical properties of the target function. One option is represented by global search processes such as "simulated annealing," genetic algorithms, multiple randomly initialized local search, etc. Alternatively, a local search process may be used if a rough initial solution is known. Examples of such are "downhill simplex," various types of gradient descent processes, etc. Any desired approximations and/or heuristics may be used for a rough initialization. For example, some of the model parameters may be assumed as known (for example, fine units of the shape of boundary surfaces), and the remaining model parameters may be determined by a complete search on a relatively rough grid. The target function is used as a reference for evaluating one or more alternative initial solutions.

A resolution hierarchy may be used for reducing the computing effort for the optimization. To this end, multiple steps having a lower resolution may be computed from the actual B scan. The search begins at the lowest resolution, and is successively increased. Thus, a global search is necessary only at the lowest resolution.

As a variant of this method step, initially any given method for determining the boundary surfaces or in general for adapting the eye model to the scan or scans may be used. In this variant, the quality criterion is used not for optimization, but, rather, only for assessing the detected surfaces or the adaptation of the eye model and the biometric measurements determined therefrom. This may be considered as a special case of the optimization which is composed only of initialization and one-time evaluation of the target function.

In a final method step, the corrected parametric eye model is represented on the user interface as an image and/or in the form of the relevant biometric measured values.

Based on the measure of quality, the scan or scans and/or the adaptation of the eye model and/or the detected boundary surfaces and/or the resulting biometric measurements may be rejected as unusable, or the user may be requested to perform a manual assessment with the options of accepting the results, redetermining manually or semiautomatically, or rejection.

The following variables of the eye in particular are regarded as relevant biometric measured values:
Central corneal thickness (CCT),
The internal and external anterior chamber depth (iACD, eACD),
The lens thickness (LT),
The length of the eye (AL),
The retinal thickness (RT),
A 2D map of the corneal thickness (pachymetry),
The volume of the anterior chamber,
The distance of the anterior chamber angle,
The depth of the equator of the lens, and
The lens tilt and decentration.

Using the present approach according to the invention, a method is provided by means of which the biometry of an eye may be easily determined, in particular also under nonideal conditions. Patient exposure to radiation may be reduced to a minimum due to a large number of reproducible and evaluatable measured values and the shortening of the measuring time.

By application of the method according to the invention based on optical coherence tomography, the determination of the biometry of eyes may be optimized significantly.

As a result of the algorithms stored in the control and evaluation unit, as well as the parametric eye model, in addition to the adaptation of this model to the scan or scans, for example by optimizing the quality criterion or target function, the proposed method may proceed semiautomatically or also fully automatically.

The invention claimed is:

1. A method of model-based determination of the biometry of eyes, based on optical coherence tomography (OCT), comprising
illuminating the eye by a light source via a scanning unit, wherein a focus of a measuring light beam in the eye is movable or switchable laterally and/or axially by application of an adjusting device;
detecting light components back-scattered from boundary surfaces and from tissue of the eye by a sensor via an interferometer;
relaying information from the sensor to a control and evaluation unit;
performing one or more scans having same or different scan patterns, same or different focus settings or a combination of the foregoing by application of the scanning unit, and receiving the scans by the sensor via the interferometer and relaying the one or more scans to the control and evaluation unit, which adapts a parametric eye model to create an adapted parametric eye model, which includes at least two boundary surfaces present in the eye;
deriving biometric measured values from the adapted parametric eye model; and
representing individual scans, all scans, the adapted parametric eye model or a combination thereof via a user interface.

2. The method according to claim 1, wherein the sensor receives B scans in the form of partial or whole eye scans via the interferometer.

3. The method according to claim 1, further comprising carrying out the adaptation of the parametric eye model to the scan or scans by the control and evaluation unit by comparing actual scans and simulated scans, by fitting functions or by a combination of comparing actual scans and simulated scans and by fitting functions.

4. The method according to claim 1, wherein the parametric eye model is two or three-dimensional, and model parameters of the adapted parametric eye model which describe the state of the eye are partially or completely configured.

5. The method according to claim 1, further comprising transmitting model parameters which are known or determined by other measuring methods via at least one of a measuring unit, an input unit or a data transmission unit which is additionally present.

6. The method according to claim 1, further wherein the control and evaluation unit compares simulated scans to actual OCT scans, and uses a determined deviation as a quality criterion of the model parameters or as a target function.

7. The method according to claim 1, further comprising taking into account via the control and evaluation unit, in at least one of the generation of simulated OCT scans, as part of the quality criterion, the target function or in the fitting of functions sources of error in at least one of signal generation, signal recording, or signal processing.

8. The method according to claim 7, further comprising optimizing the quality criterion or the target function by the control and evaluation unit, and adapting the parametric eye model to the scan or scans by the optimizing.

9. The method according to claim 7, further comprising using the partially or completely configurable model parameters in the generation of at least one of the simulated OCT scans, the quality criterion, the target function, the adaptation of the model to the actual scan or scans or in the fitting of functions, and wherein the partially or completely configurable model parameters directly influence the foregoing.

10. The method according to claim 1, further comprising using any given model for adapting the eye model to the scan or scans, and using the quality criterion not for optimization, but, rather, only for assessing the adaptation.

11. The method according to claim 1, further comprising, based on a measure of quality, rejecting the scan or scans and/or detected boundary surfaces and/or resulting biometric measurements as unusable, or requesting that the user to perform a manual assessment with the options of accepting the results, redetermining manually or redetermining semi-automatically, or rejection.

12. The method according to claim 1, further comprising representing the adapted parametric eye model on the user interface as an image, in the form of the relevant biometric measured values or both as an image and in the form of the relevant biometric measured values.

* * * * *